United States Patent [19]

Wright

[11] Patent Number: 4,946,463
[45] Date of Patent: Aug. 7, 1990

[54] VESSEL OCCLUDER

[75] Inventor: John T. M. Wright, Conifer, Colo.

[73] Assignee: Pioneering Technologies, Inc., Wheat Ridge, Colo.

[21] Appl. No.: 340,145

[22] Filed: Apr. 10, 1989

[51] Int. Cl.⁵ .......................................... A61B 17/00
[52] U.S. Cl. .................................... 606/158; 606/157
[58] Field of Search ............... 128/325, 327; 606/157, 606/158

[56] References Cited

U.S. PATENT DOCUMENTS 4,168,708  9/1979  Lepley, Jr. et al. ................ 128/325

Primary Examiner—Randall L. Green
Assistant Examiner—Gary Jackson
Attorney, Agent, or Firm—Grant L. Hubbard

[57] ABSTRACT

An improved vessel occluder that is suitable for use in coronary artery surgery, comprising two smooth bullet shaped occluders, thermoformed from extruded tubing, affixed to the each end of a monofilament, which is looped and passed through a length of radiopaque soft plastic tubing which acts as a simple holder is disclosed.

3 Claims, 1 Drawing Sheet 4,946,463

VESSEL OCCLUDER

FIELD OF THE INVENTION

This invention relates to an improved vessel occluder for use as an aid in the execution of selected cardiovascular surgical procedures, having particular applicability in coronary artery surgery.

BACKGROUND OF THE INVENTION

It is common surgical practice to use bypass grafts to help reestablish coronary artery circulation. In most patients one or usually more segments of the saphenous vein taken from the patient's legs will be implanted between the aorta near its base and just distal to the blockage of the branch of the stenosed coronary artery. In some patients, the internal mammary artery is also utilized for bypassing the most important coronary artery which is stenosed.

The aorta is cross clamped during the period of actual coronary artery surgery to minimize bleeding from the anastomotic sites of the coronary arteries. However, when an incision is made into the stenotic coronary artery, sometimes a significant amount of hemorrhage occurs. The hemorrhage is thought to be due to the presence of collateral circulatory channels, probably emanating from the bronchial arteries. In such circumstances the surgeon's delicate task of producing a competent, yet leak tight, anastomosis between the bypass graft and the semi-occluded vessel in a resonably short time, is made difficult.

The coronary artery occluder, which is the subject of this invention, is intended for use as an aid to the surgeon in this particular circumstance by preventing or minimizing hemorrhage from the coronary arteries during this procedure. The device serves to occlude the artery to minimize bleeding.

Vessel occluders are known in the art. For example Mullen, D. C., Lepley, D. Jr., and Flemma, R. J. described the use of a coronary occluder in their paper "Coronary artery surgery without global ischemia." Ann Thorac Surg 24:90, 1977. This device is a "T" shaped device with a bulbous tip placed at either end of the "T." The device was manufactured from silicon rubber.

A similar device, the Florester ® coronary artery occluder, is presently produced, and described in a brochure, by Bio-Vascular, Inc. St Paul, Minnesota. The drawback of this device is that it is expensive and is intended for multiple use. Following each use the device has to be thoroughly cleansed and re-sterilized before reuse in the next patient. The "T" configuration in which the bulbous tips are placed at opposite ends of the "T" can also cause difficulties for the surgeon. The bulbous tips of the device have to be inserted into each of the two parts of the vessel a cumulative amount equal to the distance between the tips, this distance being fixed by the configuration of the device. Normally each tip would be inserted an equal distance into the vessel, but should the anastomotic site be close to a proximal partial coronary occlusion, one tip can only be inserted a short distance before reaching the occlusive area. It follows, in such circumstances, that the second tip, being a fixed distance from the first, will have to be inserted further into the distal coronary artery than desired. Should a bifurcation be present within this distance the device could not be used. A further disadvantage of the device is that the core material of the "T" is of braided fibers coated with silicon rubber. Should the surgeon inadvertently catch and penetrate this with the suture needle the device is permanently damaged and has to be discarded.

Similar devices could be manufactured by the injection molding of a suitable thermoplastic material onto a suitable flexible suture, preferably of monofilament construction. The drawback of this approach is that while of low cost, injection molding dies involve parting or split lines in the dies, which cause "flash" on the molded parts. This "flash" takes the form of surface discontinuities, which would have to be removed before the device could safely be inserted into the lumen of a coronary artery. The removal of "molding flash" could be expensive and difficult. Any significant surface blemish on the coronary occluder would potentially cause trauma to the intima of the vessel, leading to coronary thrombosis. The device which is the subject of this invention does not have these disadvantages.

It is an objective of this invention to provide a vessel occluder which overcomes the described deficiencies in the prior art.

It is a further objective of this invention to provide a vessel occluder without significant surface defects on the vessel intima contacting surfaces.

It is a further objective of this invention to temporarily hold open the arteries during anastomosis to improve exposure of the cut ends of the vessel for the anastomosis.

It is a further objective of this invention to occlude the artery to minimize bleeding.

It is a further objective of this invention to provide a vessel occluder to occlude coronary arteries.

It is a further objective of this invention to provide a vessel occluder with bulbous tips that do not have to be inserted into the vessel a predetermined cumulative distance.

It is a further objective of this invention to provide a vessel occluder with bulbous tips connected and retailed with a monofilament member.

The simplicity and design of the vessel occluder of this invention are such that it is quite inexpensive and hence may be disposable, hereby eliminating the necessity of cleaning and sterilizing between uses. Other objectives and advantages of this invention will be more apparent from the detailed description of the device which follows.

SUMMARY OF THE INVENTION

An improved vessel occluder that is suitable for use in coronary artery surgery. The simplicity of the design and construction is such that the device can be made cheaply, and can thus be disposable. Two smooth bullet shaped occluders, thermoformed from extruded tubing, are affixed to each end of a monofilament, which is looped and passed through a length of radiopaque soft plastic tubing. This tubing acts as a simple holder. A size indicating label is attached to the loop which prevents it from being pulled through the tubing. Retention of the occluders on the monofilament is by a knot abutting a thermoformed shoulder, and by a ultra-violet setting adhesive.

This invention is directed to a vessel occluder comprising a bullet shaped radiopaque plastic member, firmly affixed to each end of a monofilament suture. The monofilament is looped, passed through a suitable length of soft radiopaque plastic tubing, and a sizing label attached to the mid point of the loop. The device will be made available in various sizes.

DETAILED DESCRIPTION OF THE DRAWINGS

For the purpose of illustrating the invention, there is shown the form which is presently preferred; it being understood, however, that this invention is not limited to the precise arrangements and instrumentalities shown.

DETAILED DESCRIPTION OF THE INVENTION

Figure 1:
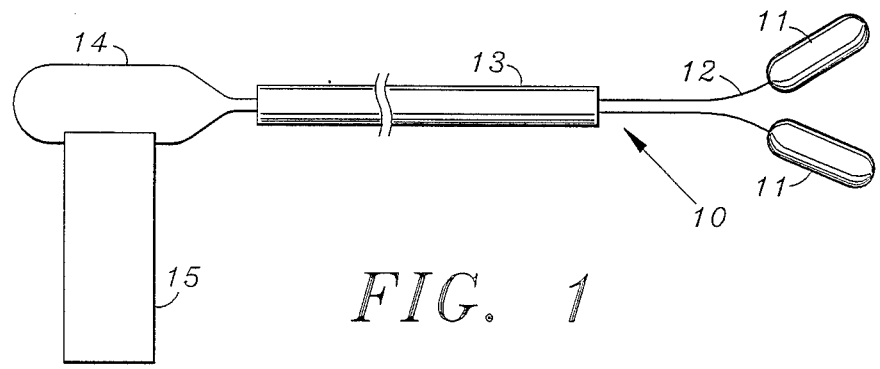
FIG. 1 is a plan view of the vessel occluding device.
Figure 2:
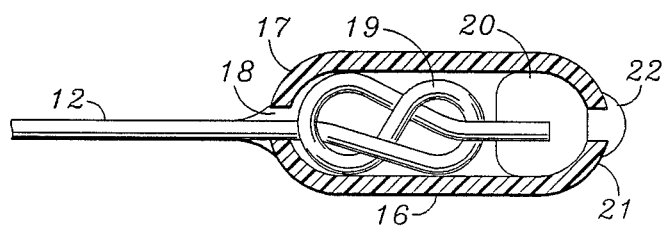
FIG. 2 is an enlarged part sectional view of the preferred embodiment of the device showing the construction of the bullet shaped member, and the methods of attachment to the monofilament member.

Referring to the drawings wherein like numerals indicate like elements there is shown in FIG. 1 a vessel occluder designated as 10, composed of two bullet shaped members 11, each affixed to a monofilament 12. The monofilament passes through a length of flexible tubing 13, forming a loop 14. Attached to the loop is a label 15, which serves to designate the diameter of the bullet shaped members 11, and also prevent the loop 14 from being pulled thorough tubing 13. Referring to FIG. 2, each bullet shaped vessel occluder is made of a short section of extruded, medical grade, radiopaque polyurethane tubing 16. One end of the tube is thermoformed into a nearly closed configuration 17, leaving a small hole 18. Thermoforming may be carried out by placing the square cut end of the plastic tube into a suitable circular recess in a heated metal block. The tube is rotated and an axial load is applied. As the end of the tube is heated and softens, the rotation and axial load causes deformation. The thermoformed end is then removed from the heated recess and allowed to cool. Suitable control of temperature, rotational speed and axial load and time of application will control the amount of deformation that will take place for certain tube dimensions and compositions.

A suitable length of a surgical grade monofilament, such as a 2.0 Black Nylon monofilament suture, is threaded through hole 18. A figure-of-eight knot 19 is tied at the end of the suture. A small quantity of medical grade adhesive 20, preferably an ultra-violet light setting adhesive, is applied to the knot 19, which is then pulled inside the tube to rest snugly against the theroformed end of the tube 18. Any excessive adhesive is removed from the outer end of the tube. The adhesive is cured in approximately 10 seconds by exposure to ultra violet light of suitable intensity and wavelength. Such high intensity ultra-violet radiation is able to penetrate the tubing and effect the cure. The open end of the tube is then thermoformed closed 21, and the central area sealed with a small quantity 22 of the same adhesive. A similar occluder is attached to the other end of the monofilament. The monofilament is then looped 14, and passed through the flexible plastic tubing 13. This soft tubing acts as a simple holder allowing the surgeon easily to position the device. The size indicating label 15 is applied to the loop. The plastic tubing 13 is shorter than the length of the monofilament between the label and the proximal edges of the occluder. Within limits defined by the excess length of the looped monofilament compared to the length of the plastic tubing, each occluder is able to be positioned in the vessel independent of the position of the other.

Figure 3:
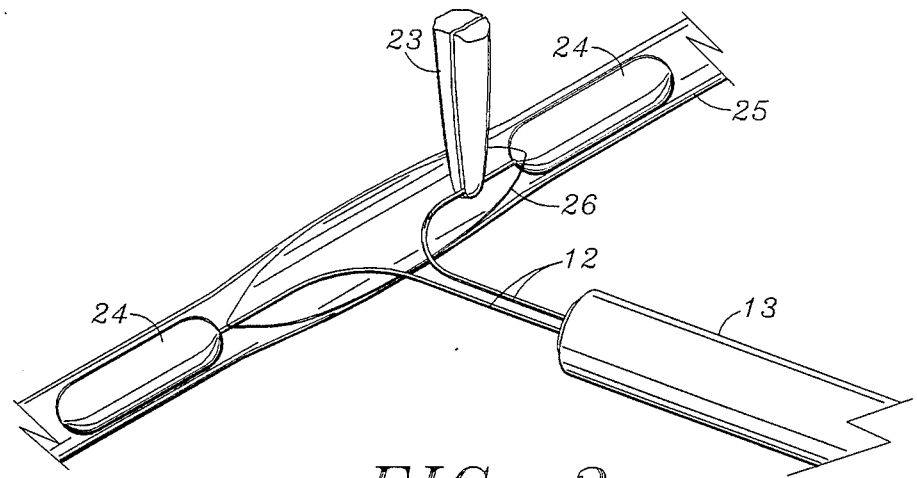
FIG. 3 is an isometric view showing the use of the device for coronary artery anastomoses.

In use, following commencement of cardio-pulmonary bypass, the heart will usually be immobilized by cross clamping the base of the aorta, and perfusing cold cardioplegia solution into the coronary arteries via the aortic root. The surgeon makes a suitable incision into the lumen of the coronary artery to be bypassed, distal to the coronary occlusion, and elongates the incision as required. A coronary probe is then inserted into the vessel to check for occlusions, and to estimate the diameter of the lumen of the lumen of the vessel. The appropriate size of coronary occluder is selected. The size selected will be such that the bullet shaped occluders may be gently but firmly inserted into the lumen of the artery. Referring to FIG. 3, using atraumatic forceps 23 to grip the monofilament close to the occluder 11, the occluders are pushed into the exposed lument 24, slightly past the area of the incision 25. The firmly fitting occluder will prevent hemorrhage from the artery, and serve to hold the vessel in a circular configuration, thus improving exposure for the surgeon to place the anastomotic sutures. The anastomosis of the saphenous vein or the internal mammary artery is carried out in the usual manner. Prior to completing the anastomosis by typing off the anastomotic suture, each occluder is, in turn, gently removed using atraumatic forceps to grip the monofilament in a suitable place, and pulling gently.

The devices may be provided with occludes of sizes appropriate to surgical demands. The instrumentation required for proper size selection of these vessel occluders consists of vessel probes. These cardiovascular surgical instruments are available in suitable sizes and have been used routinely in coronary artery sugery for many years.

It will be understood that variations in materials, manufacturing techniques, etc, as well as in size and precise configuration may be made without departing from the invention.

INDUSTRIAL APPLICATION

This invention is useful in veterinary and human surgical procedures.

What is claimed is:

1. An improved vessel occluder for preventing or minimizing the hemorrhage of vessels during surgery of the type wherein two occluders are connected together, the improvement wherein:
   (a) both occluding members are thermoformed from extruded plastic tubing having a diameter of from about 1.0 to 6.0 mm, each end of the occluding members configured to define a rounded bullet shape;
   (b) the occluding members are attached to each other by a monofilament having a knot formed in each of the respective occluding members and a biocompatible adhesive bonding the knots to the members, to secure such members, respectively, to the respective ends of the monofilament.

2. A method of manufacturing an improved vessel occluder for preventing or minimizing the hemorrhage of vessels during surgery of the type wherein two occluders are connected together, comprising the steps of:
   (a) thermoforming each occluder from extruded plastic tubing having a diameter of from about 1.0 to 6.0 mm;

(b) forming each end of the occluding members to define a rounded bullet shape; and (b) attaching the occluding members to each other by a monofilament by positioning a knot in each of the respective occluding members.

3. The method of claim 2 further comprising the step of adhesively bonding the knot in each of the occluding members using biocompatible adhesive.